(12) United States Patent
Colavito et al.

(10) Patent No.: US 12,186,182 B2
(45) Date of Patent: *Jan. 7, 2025

(54) VALVED CONDUIT

(71) Applicant: EDWARDS LIFESCIENCES CORPORATION, Irvine, CA (US)

(72) Inventors: Kyle W. Colavito, Flagstaff, AZ (US); Edwin W. Field, Flagstaff, AZ (US); Colin T. Burns-Heffner, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 391 days.

This patent is subject to a terminal disclaimer.

(21) Appl. No.: 17/314,484

(22) Filed: May 7, 2021

(65) Prior Publication Data

US 2021/0322158 A1  Oct. 21, 2021

Related U.S. Application Data

(63) Continuation of application No. 16/129,673, filed on Sep. 12, 2018, now Pat. No. 11,039,919.

(Continued)

(51) Int. Cl.
  *A61F 2/24* (2006.01)
  *A61L 27/56* (2006.01)

(52) U.S. Cl.
  CPC .......... *A61F 2/2418* (2013.01); *A61F 2/2412* (2013.01); *A61F 2/2415* (2013.01); *A61F 2/2475* (2013.01); *A61L 27/56* (2013.01); *A61F 2/2409* (2013.01); *A61F 2/2427* (2013.01); *A61F 2210/0076* (2013.01); *A61F 2220/0008* (2013.01); *A61F 2220/005* (2013.01);

(Continued)

(58) Field of Classification Search
  CPC .... A61F 2/2418; A61F 2/2415; A61F 2/2409; A61F 2/2427; A61F 2210/0076; A61F 2220/0008; A61F 2220/0075; A61F 2230/0069; A61L 27/56
  See application file for complete search history.

(56) References Cited

U.S. PATENT DOCUMENTS

| 4,759,759 A | 7/1988 | Walker et al. |
| 5,037,434 A | 8/1991 | Lane |

(Continued)

FOREIGN PATENT DOCUMENTS

| CN | 101361683 A | 2/2009 |
| CN | 101754729 A | 6/2010 |

(Continued)

OTHER PUBLICATIONS

International Preliminary Report on Patentability received for PCT Patent Application No. PCT/US2015/066865, dated Jun. 29, 2017, 7 pages.

(Continued)

*Primary Examiner* — Suzette J Gherbi

(74) *Attorney, Agent, or Firm* — Alan T. Hale; CHANG & HALE LLP

(57) ABSTRACT

Various aspects of the present disclosure are directed toward apparatuses, systems, and methods that include a valved conduit. The valved conduit may include at least one leaflet and an interior surface that mitigates against thrombus formation within the conduit.

16 Claims, 8 Drawing Sheets

Related U.S. Application Data

(60) Provisional application No. 62/579,752, filed on Oct. 31, 2017.

(52) U.S. Cl.
CPC ............. *A61F 2220/0058* (2013.01); *A61F 2220/0075* (2013.01); *A61F 2230/0069* (2013.01)

(56) References Cited

U.S. PATENT DOCUMENTS

| | | |
|---|---|---|
| 5,163,955 A | 11/1992 | Love et al. |
| 5,708,044 A | 1/1998 | Branca |
| 5,713,953 A | 2/1998 | Vallana et al. |
| 5,861,028 A | 1/1999 | Angell |
| 5,928,281 A | 7/1999 | Huynh et al. |
| 5,935,163 A | 8/1999 | Gabbay |
| 6,074,419 A | 6/2000 | Healy et al. |
| 6,086,612 A | 7/2000 | Jansen |
| 6,171,335 B1 | 1/2001 | Wheatley et al. |
| 6,174,331 B1 | 1/2001 | Moe et al. |
| 6,197,143 B1 | 3/2001 | Bodnar |
| 6,254,636 B1 | 7/2001 | Peredo |
| 6,283,995 B1 | 9/2001 | Moe et al. |
| 6,287,338 B1 | 9/2001 | Sarnowski et al. |
| 6,334,873 B1 | 1/2002 | Lane et al. |
| 6,364,905 B1 | 4/2002 | Simpson et al. |
| 6,432,542 B1 | 8/2002 | Tsai |
| 6,541,589 B1 | 4/2003 | Baillie |
| 6,562,069 B2 | 5/2003 | Cai et al. |
| 6,613,086 B1 | 9/2003 | Moe et al. |
| 6,613,087 B1 | 9/2003 | Healy |
| 6,696,526 B1 | 2/2004 | Kaulbach et al. |
| 6,951,571 B1 | 10/2005 | Srivastava |
| 6,994,666 B2 | 2/2006 | Shannon et al. |
| 7,018,404 B2 | 3/2006 | Holmberg et al. |
| 7,261,732 B2 | 8/2007 | Justino |
| 7,306,729 B2 | 12/2007 | Bacino et al. |
| 7,320,705 B2 | 1/2008 | Quintessenza |
| 7,331,993 B2 | 2/2008 | White |
| 7,361,189 B2 | 4/2008 | Case et al. |
| 7,462,675 B2 | 12/2008 | Chang et al. |
| 7,531,611 B2 | 5/2009 | Sabol et al. |
| 7,604,663 B1 | 10/2009 | Reimink et al. |
| 7,833,565 B2 | 11/2010 | O'Connor et al. |
| 7,862,610 B2 | 1/2011 | Quintessenza |
| 8,216,631 B2 | 7/2012 | O'Connor et al. |
| 8,219,229 B2 | 7/2012 | Cao et al. |
| 8,246,676 B2 | 8/2012 | Acosta et al. |
| 8,267,994 B2 | 9/2012 | Jin |
| 8,303,647 B2 | 11/2012 | Case |
| 8,409,274 B2 | 4/2013 | Li et al. |
| 8,556,960 B2 | 10/2013 | Agnew et al. |
| 8,637,144 B2 | 1/2014 | Ford |
| 8,801,779 B2 | 8/2014 | Seguin et al. |
| 8,834,911 B2 | 9/2014 | Glezer et al. |
| 8,961,593 B2 | 2/2015 | Bonhoeffer et al. |
| 8,961,599 B2 | 2/2015 | Bruchman et al. |
| 8,992,608 B2 | 3/2015 | Haug et al. |
| 9,139,669 B2 | 9/2015 | Xu et al. |
| 9,155,610 B2 | 10/2015 | Soletti et al. |
| 9,155,618 B2 | 10/2015 | Kalmann et al. |
| 9,259,313 B2 | 2/2016 | Wheatley |
| 9,301,835 B2 | 4/2016 | Campbell et al. |
| 9,301,837 B2 | 4/2016 | Beith |
| 9,364,322 B2 | 6/2016 | Conklin et al. |
| 9,504,568 B2 | 11/2016 | Ryan et al. |
| 9,539,089 B2 | 1/2017 | Beith |
| 9,579,196 B2 | 2/2017 | Morriss et al. |
| 9,622,862 B2 | 4/2017 | Lashinski et al. |
| 9,636,219 B2 | 5/2017 | Keidar et al. |
| 9,655,720 B2 | 5/2017 | Bluestein et al. |
| 9,675,453 B2 | 6/2017 | Guttenberg et al. |
| 9,717,593 B2 | 8/2017 | Alkhatib et al. |
| 9,833,314 B2 | 12/2017 | Corbett |
| 9,855,141 B2 * | 1/2018 | Dienno ................. A61F 2/2418 |
| 9,937,037 B2 | 4/2018 | Dienno et al. |
| 9,987,120 B2 | 6/2018 | Soletti et al. |
| 9,999,500 B2 | 6/2018 | Greenslet et al. |
| 10,052,200 B2 | 8/2018 | Chung et al. |
| 10,195,023 B2 | 2/2019 | Wrobel |
| 10,299,915 B2 | 5/2019 | Edelman et al. |
| 10,413,402 B2 | 9/2019 | Squara |
| 10,413,403 B2 | 9/2019 | Boden et al. |
| 10,426,609 B2 | 10/2019 | Edelman et al. |
| 10,433,955 B2 | 10/2019 | Edelman et al. |
| 10,500,040 B2 * | 12/2019 | Hacohen ............... A61F 2/2469 |
| 10,512,537 B2 | 12/2019 | Corbett et al. |
| 10,588,746 B2 | 3/2020 | Bernstein et al. |
| 10,603,164 B2 | 3/2020 | Girard et al. |
| 10,695,170 B2 | 6/2020 | Conklin et al. |
| 10,799,342 B2 | 10/2020 | Danino |
| 11,039,919 B2 * | 6/2021 | Colavito ................. A61L 27/56 |
| 11,090,460 B2 | 8/2021 | Jaroch et al. |
| 11,109,963 B2 * | 9/2021 | Dienno ................. A61F 2/2412 |
| 11,833,034 B2 * | 12/2023 | Argento ............... A61F 2/2418 |
| 2002/0032487 A1 | 3/2002 | Dua et al. |
| 2002/0198594 A1 | 12/2002 | Schreck |
| 2003/0027332 A1 | 2/2003 | Lafrance et al. |
| 2003/0109923 A1 | 6/2003 | Chinn et al. |
| 2004/0215333 A1 | 10/2004 | Duran et al. |
| 2005/0085900 A1 * | 4/2005 | Case ..................... A61F 2/2475 623/1.24 |
| 2005/0228487 A1 | 10/2005 | Kujawski |
| 2005/0234546 A1 | 10/2005 | Nugent et al. |
| 2005/0261759 A1 * | 11/2005 | Lambrecht ............ A61F 2/2412 623/1.26 |
| 2006/0015171 A1 | 1/2006 | Armstrong |
| 2006/0109923 A1 | 5/2006 | Cai et al. |
| 2006/0136052 A1 | 6/2006 | Vesely |
| 2006/0276888 A1 | 12/2006 | Lee et al. |
| 2007/0208417 A1 | 9/2007 | Agnew |
| 2008/0071361 A1 | 3/2008 | Tuval et al. |
| 2008/0082161 A1 | 4/2008 | Woo |
| 2008/0091261 A1 | 4/2008 | Long et al. |
| 2008/0133005 A1 * | 6/2008 | Andrieu ............... A61F 2/2418 623/2.13 |
| 2008/0200977 A1 | 8/2008 | Paul et al. |
| 2008/0312737 A1 | 12/2008 | Jin |
| 2008/0319538 A1 | 12/2008 | Styrc |
| 2009/0112309 A1 | 4/2009 | Jaramillo et al. |
| 2009/0157175 A1 | 6/2009 | Benichou |
| 2009/0240320 A1 | 9/2009 | Tuval et al. |
| 2009/0299469 A1 | 12/2009 | Kollar |
| 2010/0082094 A1 | 4/2010 | Quadri et al. |
| 2010/0114307 A1 | 5/2010 | Agnew et al. |
| 2010/0131056 A1 | 5/2010 | Lapeyre |
| 2010/0161040 A1 | 6/2010 | Braido et al. |
| 2010/0168839 A1 | 7/2010 | Braido et al. |
| 2010/0185277 A1 | 7/2010 | Braido et al. |
| 2011/0112620 A1 | 5/2011 | Du George |
| 2011/0257738 A1 | 10/2011 | Corbett et al. |
| 2011/0270388 A9 * | 11/2011 | Stevens ................. A61M 25/10 623/2.11 |
| 2011/0276128 A1 | 11/2011 | Cao et al. |
| 2011/0282440 A1 | 11/2011 | Cao et al. |
| 2012/0253453 A1 | 10/2012 | Bruchman et al. |
| 2012/0323315 A1 | 12/2012 | Bruchman et al. |
| 2013/0046379 A1 | 2/2013 | Paolitto et al. |
| 2013/0172991 A1 | 7/2013 | Rolando et al. |
| 2013/0245753 A1 | 9/2013 | Alkhatib |
| 2013/0268066 A1 | 10/2013 | Rowe |
| 2013/0282114 A1 | 10/2013 | Schweich et al. |
| 2013/0304199 A1 | 11/2013 | Sutton et al. |
| 2013/0310928 A1 | 11/2013 | Morriss et al. |
| 2013/0325111 A1 | 12/2013 | Campbell et al. |
| 2014/0005776 A1 | 1/2014 | Braido et al. |
| 2014/0012371 A1 | 1/2014 | Li |
| 2014/0018915 A1 | 1/2014 | Biadillah et al. |
| 2014/0031927 A1 | 1/2014 | Bruchman et al. |
| 2014/0066897 A1 | 3/2014 | Campbell et al. |
| 2014/0128960 A1 | 5/2014 | Greenslet et al. |
| 2014/0128967 A1 | 5/2014 | Jarvik |

(56) References Cited

U.S. PATENT DOCUMENTS

| | | |
|---|---|---|
| 2014/0128968 A1 | 5/2014 | Benichou et al. |
| 2014/0148897 A1 | 5/2014 | Matheny |
| 2014/0214158 A1 | 7/2014 | Board et al. |
| 2014/0243958 A1 | 8/2014 | Yang et al. |
| 2014/0324160 A1 | 10/2014 | Benichou et al. |
| 2015/0119980 A1 | 4/2015 | Beith et al. |
| 2015/0224231 A1 | 8/2015 | Bruchman et al. |
| 2016/0015516 A1 | 1/2016 | Bernstein et al. |
| 2016/0067032 A1 | 3/2016 | Soletti et al. |
| 2016/0074161 A1 | 3/2016 | Bennett |
| 2016/0100939 A1 | 4/2016 | Armstrong et al. |
| 2016/0153591 A1 | 6/2016 | Fonfara et al. |
| 2016/0175095 A1 | 6/2016 | Dienno et al. |
| 2016/0175096 A1* | 6/2016 | Dienno ............... A61F 2/2415 623/2.13 |
| 2016/0245432 A1 | 8/2016 | Fonfara et al. |
| 2016/0296322 A1 | 10/2016 | Edelman et al. |
| 2016/0331528 A1 | 11/2016 | Parker et al. |
| 2017/0000610 A1 | 1/2017 | Eppihimer et al. |
| 2017/0014227 A1 | 1/2017 | Boden et al. |
| 2017/0071729 A1 | 3/2017 | Wrobel |
| 2017/0079779 A1* | 3/2017 | Tabor ............... A61F 2/2409 |
| 2017/0079782 A1 | 3/2017 | Beith |
| 2017/0119523 A1 | 5/2017 | Cao et al. |
| 2017/0156854 A1 | 6/2017 | Hammer |
| 2017/0189175 A1 | 7/2017 | Justino et al. |
| 2017/0245989 A1 | 8/2017 | Bluestein et al. |
| 2017/0252156 A1 | 9/2017 | Bernstein et al. |
| 2018/0049872 A1 | 2/2018 | Bennett |
| 2018/0133002 A1 | 5/2018 | Yi et al. |
| 2018/0177592 A1* | 6/2018 | Benichou ............... A61F 2/2412 |
| 2018/0263775 A1 | 9/2018 | Shah |
| 2018/0344455 A1* | 12/2018 | Hacohen ............... A61F 2/2409 |
| 2018/0344457 A1* | 12/2018 | Gross ............... A61F 2/246 |
| 2019/0015191 A1 | 1/2019 | Berdajs |
| 2019/0046317 A1 | 2/2019 | Murad et al. |
| 2019/0091014 A1 | 3/2019 | Arcaro et al. |
| 2019/0091015 A1 | 3/2019 | Dienno et al. |
| 2019/0125529 A1 | 5/2019 | Colavito et al. |
| 2019/0125530 A1 | 5/2019 | Arcaro et al. |
| 2019/0125531 A1 | 5/2019 | Bennett et al. |
| 2019/0282360 A1* | 9/2019 | Colavito ............... A61F 2/2418 |
| 2019/0343617 A1 | 11/2019 | Sobrino-Serrano et al. |
| 2019/0365531 A1 | 12/2019 | Beith |
| 2020/0113681 A1* | 4/2020 | Armstrong ............ A61F 2/2415 |
| 2020/0121454 A1* | 4/2020 | Spence ............... A61F 2/2409 |
| 2020/0352705 A1 | 11/2020 | Heneghan et al. |
| 2021/0228350 A1 | 7/2021 | Dienno et al. |
| 2021/0322158 A1* | 10/2021 | Colavito ............... A61F 2/2475 |
| 2022/0087817 A1* | 3/2022 | Dasi ............... A61L 27/16 |
| 2022/0133474 A1* | 5/2022 | Bui ............... A61F 2/2433 623/2.17 |
| 2022/0226109 A1 | 7/2022 | Colavito et al. |
| 2023/0218395 A1* | 7/2023 | Murray ............... A61F 2/2418 623/2.11 |

FOREIGN PATENT DOCUMENTS

| | | |
|---|---|---|
| CN | 103800952 A | 5/2014 |
| CN | 106794065 A | 5/2017 |
| GB | 2513194 A | 10/2014 |
| JP | 2000-513248 A | 10/2000 |
| JP | 2002-525169 A | 8/2002 |
| JP | 2005-500101 A | 1/2005 |
| JP | 2007-521125 | 8/2007 |
| JP | 2010-540079 A | 12/2010 |
| JP | 2012-504031 A | 2/2012 |
| JP | 2013-540467 A | 11/2013 |
| JP | 2014-517720 A | 7/2014 |
| JP | 2015-039515 A | 3/2015 |
| JP | 2017-538518 A | 12/2017 |
| JP | 6616418 B2 | 12/2019 |
| WO | 00/18333 A1 | 4/2000 |
| WO | 00/23006 A1 | 4/2000 |
| WO | 2001/066037 A2 | 9/2001 |
| WO | 02/49540 A2 | 6/2002 |
| WO | 2003/007795 A2 | 1/2003 |
| WO | 2008/121380 A1 | 10/2008 |
| WO | 2008/133852 A1 | 11/2008 |
| WO | 2009/042196 A2 | 4/2009 |
| WO | 2009/108355 A1 | 9/2009 |
| WO | 2010/037141 A1 | 4/2010 |
| WO | 2011/147849 A1 | 12/2011 |
| WO | 2012/018779 A2 | 2/2012 |
| WO | 2012/032187 A1 | 3/2012 |
| WO | 2013/096854 A3 | 8/2013 |
| WO | 2014/145811 A1 | 9/2014 |
| WO | 2015/014960 A1 | 2/2015 |
| WO | 2016/100913 A1 | 6/2016 |
| WO | 2016/205773 A1 | 12/2016 |
| WO | 2018/150392 A1 | 8/2018 |
| WO | 2018/187714 A1 | 10/2018 |
| WO | 2019/154927 A1 | 8/2019 |
| WO | 2019/178581 A1 | 9/2019 |

OTHER PUBLICATIONS

International Search Report and Written Opinion received for PCT Patent Application No. PCT/US2015/066865, dated Mar. 22, 2016, 10 pages.

International Search Report and Written Opinion received for PCT Patent Application No. PCT/US2020/031597, dated Jul. 1, 2020, 15 pages.

Office Action for Japanese Patent Application No. 2018-228319, dated Dec. 10, 2019, 5 pages (includes original and translation).

Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.

International Preliminary Report on Patentability received for PCT Patent Application No. PCT/US2015/055348, dated Apr. 27, 2017, 18 pages.

International Preliminary Report on Patentability received for PCT Patent Application No. PCT/US2018/050771, dated May 14, 2020, 12 pages.

International Search Report and Written Opinion received for PCT Patent Application No. PCT/US2015/055348, dated Apr. 11, 2016, 23 pages.

International Search Report and Written Opinion received for PCT Patent Application No. PCT/US2018/050771, dated Feb. 25, 2019, 16 pages.

Miyazaki, et al., Expanded polytetrafluoroethylene conduits and patches with bulging sinuses and fan-shaped valves in right ventricular outflow tract reconstruction: Multiceneter study in Japan. The Journal of Thoracic and Cardiovascular Surgery, Nov. 2011, vol. 142, No. 5, pp. 1122-1129.

Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.

Ootaki et al., Medium-term outcomes after implantation of expanded polytetrafluoroethylene valved conduit. The Annals of Thoracic Surgery, 2018; 105 (3), pp. 843-850.

Shinkawa et al., Valved polytetrafluoroethylene conduits for right ventricular outflow tract reconstruction. The Annals of Thoracic Surgery. Jul. 2015; 100(1), pp. 129-137.

Understanding Your Heart Valve. Medtronic USA, Inc., 2006. Pamphlet.

Yamagishi et al. Outflow reconstruction of tetralogy of fallot using a Gore-Tex valve. The Anals of Thoracic Surgery, Dec. 1993; 56(6), pp. 1414-1417.

* cited by examiner

VALVED CONDUIT

CROSS-REFERENCE TO RELATED APPLICATION

This application is a continuation of U.S. application Ser. No. 16/129,673, filed Sep. 12, 2018, which claims the benefit of Provisional Application No. 62/579,752, filed Oct. 31, 2017, which are incorporated herein by reference in their entireties for all purposes.

FIELD

The present disclosure relates generally to prosthetic valves and more specifically to apparatuses, systems, and methods that include conduits having a valve structure therein.

BACKGROUND

Bioprosthetic heart valves have been developed that attempt to mimic the function and performance of a native valve. Flexible leaflets may be mechanically coupled to a relatively rigid frame that supports the leaflets and provides dimensional stability when implanted. Although bioprosthetic heart valves can provide excellent hemodynamic and biomechanical performance in the short term, they are prone to calcification and cusp tears, among other failure modes, requiring reoperation and replacement.

The leaflets typically require some means for securing the leaflets to a support structure. In operation, the leaflets open when the upstream fluid pressure exceeds the downstream fluid pressure and close when the downstream fluid pressure exceeds the upstream fluid pressure. The leaflet free edges of the leaflets coapt under the influence of downstream fluid pressure closing the prosthetic heart valve to prevent downstream blood from flowing retrograde through the prosthetic heart valve.

Prosthetic heart valve durability under the repetitive loads of the leaflets opening and closing is dependent, in part, on the load distribution between the leaflet and the frame and attachment of the leaflet to the frame. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material.

A number of fabrication techniques have been used to couple leaflets to the inside of a conduit, however, the fabrication techniques may be labor intensive and/or failure prone. In addition, mechanical fixation of leaflets, for example as shown in U.S. Publication No. 2016/00100939, may contribute to thrombus formation. As a result, there is a significant need for a valved conduit, encompassing a conduit and a valve structure, with long durability and easier manufacture.

SUMMARY

Described embodiments are directed to apparatus, system, and methods for valved conduits.

According to one example ("Example 1"), a valved conduit includes a conduit having an interior surface and an exterior surface; and at least one leaflet having an external portion non-mechanically adhered to the exterior surface of the conduit and an internal portion arranged within the interior surface of the conduit to mitigate against thrombus formation within the conduit.

According to another example ("Example 2") further to Example 1, the external portion of the at least one leaflet is adhered to the exterior surface of the conduit by adhesive, thermal bonding, or chemical bonding.

According to another example ("Example 3") further to any one of Examples 1-2, the conduit is free of sinuses.

According to another example ("Example 4") further to any one of Examples 1-2, the conduit is free of mechanical coupling.

According to another example ("Example 5") further to any one of Examples 1-4, the external portion of the at least one leaflet is attached to the exterior surface of the conduit, and the attachment is sutureless.

According to another example ("Example 6") further to any one of Examples 1-5, the external portion of the at least one leaflet is adhered to the exterior surface of the conduit by a layer of adhesive film.

According to another example ("Example 7") further to Example 6, wherein the adhesive film is arranged about a circumference of the conduit.

According to another example ("Example 8") further to any one of Examples 6-7, further including a flexible film arranged about the circumference of the conduit and the adhesive film.

According to another example ("Example 9") further to Example 8, the flexible film includes expanded Polytetrafluoroethylene (ePTFE) and the adhesive film comprises fluorinated ethylene propylene (FEP).

According to another example ("Example 10") further to any one of Examples 8-9, further including a support frame coupled to the conduit by the flexible film.

According to another example ("Example 11") further to Example 10, the support frame is formed of Polyether ether ketone (PEEK).

According to another example ("Example 12") further to any one of Examples 1-11, further including at least one radiopaque markers arranged adjacent to the at least one leaflet on the exterior surface of the conduit.

According to another example ("Example 13") further to any one of Examples 1-12, the interior surface of the conduit is diametrically constant and free of any macroscopic interruptions.

According to another example ("Example 14") further to any one of Examples 1-13, the at least one leaflet is positioned within the conduit at a longitudinal location along the length of the conduit, and the conduit is diametrically constant at the longitudinal location where the at least one leaflet is positioned and through adjacent proximal and distal portions of the conduit.

According to one example ("Example 15"), a valved conduit includes a conduit having an interior surface, an exterior surface, a proximal portion, and a distal portion; a leaflet attachment portion having an opening between the interior surface and the exterior surface of the conduit; and at least one leaflet having an attachment section attached to the exterior surface of the conduit without mechanical alteration of the interior surface or the exterior surface of the conduit to mitigate against thrombus formation within the conduit.

According to another example ("Example 16") further to Example 15, the at least one leaflet includes three leaflets, and the three leaflets are separated from one another within the interior of the conduit by gaps.

According to another example ("Example 17") further to Example 16, the conduit includes commissure gaps separating the leaflets at the attachment section of each of the leaflets to form the gaps between the three leaflets within the interior surface of the conduit.

According to another example ("Example 18") further to any one of Examples 15-17, the attachment section is attached to the exterior surface of the conduit by an adhesive, thermal bonding, or chemical bonding.

According to another example ("Example 19") further to any one of Examples 15-18, the attachment section includes a first portion and a second portion, and the first portion is attached to the proximal portion of the exterior surface of the conduit, and the second portion is attached to the distal portion of the exterior surface of the conduit.

According to another example ("Example 20") further to any one of Examples 15-19, the leaflet attachment portion is a portion of the conduit, and the leaflet attachment portion is denser than remaining portions of the conduit.

According to one example ("Example 21"), further to any one of Examples 15-20, the valved conduit also includes a directional indicator on the exterior surface of the conduit to indicate the direction of blood flow within the conduit.

According to one example ("Example 22"), a method for reducing thrombus formation arising from the replacement of the native pulmonary valve or of a previously implanted pulmonary valved conduit where partial or complete reconstruction of the right ventricular outflow tract and/or main pulmonary artery is desired, the method includes the steps of: providing a medical device comprising a synthetic conduit having a distal end, proximal end, an interior, an exterior, and a leaflet attachment portion and at least one flexible synthetic leaflet having a portion external to the conduit and a portion internal to the conduit; wherein the leaflet portion external to the conduit is attached to the exterior of the conduit at the attachment portion and wherein the attachment portion of the conduit is free of punctures; and surgically implanting the medical device.

According to one example ("Example 23"), a method for the replacement of the native pulmonary valve or of a previously implanted pulmonary valved conduit where partial or complete reconstruction of the right ventricular outflow tract and/or main pulmonary artery is desired, the method includes the steps of: providing a medical device comprising a synthetic conduit and at least one flexible synthetic valve leaflet attached to the synthetic conduit that has been rinsed in saline and has not been pre-clotted; and surgically implanting the medical device.

According to one example ("Example 24"), a method for the replacement of the native pulmonary valve or of a previously implanted pulmonary valved conduit where partial or complete reconstruction of the right ventricular outflow tract and/or main pulmonary artery is desired, the method includes the steps of: providing a medical device that has been rinsed in saline and has not been pre-clotted, wherein said medical device comprises a non-biological conduit and at least one flexible polymeric non-biological valve leaflet attached to the non-biological conduit; identifying the inflow and outflow regions of the medical device; accessing the intended position with respect to the coronary arteries to assure there is no risk of coronary compression when implanted; optionally trimming the inflow and or outflow conduit, while under moderate tension, to the appropriate length for implantation; and attaching the medical device.

According to one example ("Example 25"), a packaging insert for a valved conduit, the packaging insert includes: a support structure configured to fold to form one or more supports and to insert within the valved conduit to support one or more leaflets within the valved conduit.

The foregoing Examples are just that, and should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1B:
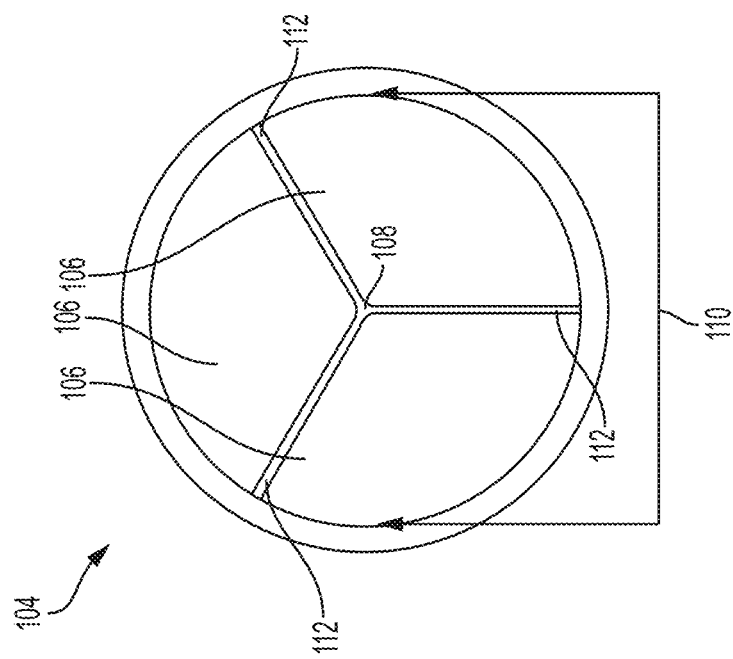
FIG. 1B illustrates an interior downstream view of a valve structure in a closed configuration, as shown in FIG. 1A.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valved conduits. However, embodiments within the scope of this disclosure can be applied toward any valved conduit, valve structure, or mechanism of similar structure and/or function. Furthermore, embodiments within the scope of this disclosure can be applied in non-cardiac applications.

Embodiments herein include various apparatuses, systems, and methods for a conduit having a valve structure operable as a prosthetic valve that can be used, such as, but not limited to, replace a pulmonary valve and a portion of the corresponding pulmonary artery. The valve structure may include one or more leaflets operable as a one-way valve with the conduit defining a conduit lumen. The leaflet(s) open to permit flow and close to occlude the conduit lumen and prevent flow in response to differential fluid pressure.

Figure 1A:
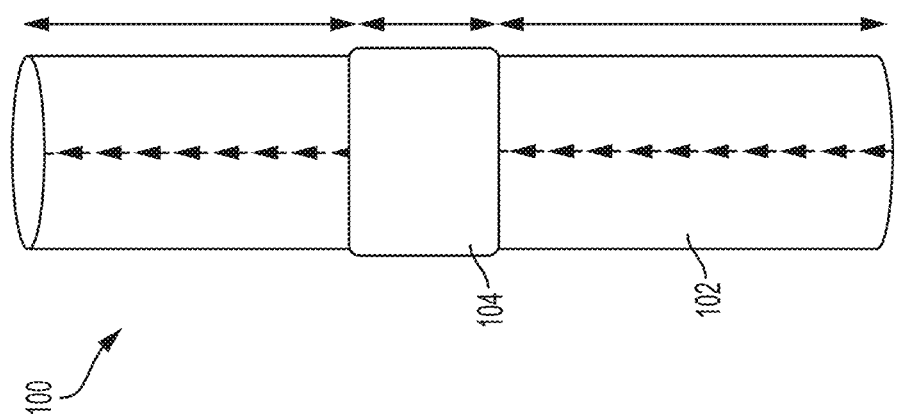
FIG. 1A is an illustration of an example valved conduit, in accordance with an embodiment.

FIG. 1A is an illustration of an example valved conduit 100, in accordance with an embodiment. The valved conduit 100 includes a conduit 102 with a valve structure 104 arranged within the conduit 102. The conduit 102 may include an upstream end and a downstream end such that the valve structure 104 allows flow in one direction.

The valved conduit 100 may be used, in a non-limiting example, as a shunt for connecting of the right ventricle to the pulmonary artery following a Norwood operation, as frequently performed for the treatment of hypoplastic left heart syndrome. In one non-limiting example, the valved conduit 100 may be indicated for the correction or reconstruction of the right ventricle outflow tract (RVOT) in pediatric patients. Such reconstruction may be indicated for congenital heart disorders such as tetralogy of Fallot, Truncus Arterious, Dextro-Transposition of the Great Arteries, Pulmonary Atresia of Intact Ventricular Septum, or Aortic Valvular Disease. The valved conduit 100 may also be indicated for the replacement of previously implanted homografts or valved conduits that have become dysfunctional or insufficient. In addition, the valved conduit 100 may have applications in treating a wider range of heart disorders, including other areas of the heart. Generally, the term "distal" is used in the disclosure to refer to the outflow end (distal end) or outflow direction of a valved conduit 100, and in turn the term "proximal" is used to refer to the inflow end of a valved conduit 100, or a direction opposite the direction of primary flow through the valved conduit 100.

FIG. 1B illustrates an interior downstream view of a valve structure 104 in a closed configuration, as shown in FIG. 1A. The valve structure 104 includes leaflets 106 that extend into an interior of the conduit 102. Although three leaflets 106 are shown in FIG. 1B, the valve structure 104 may include one, two, four, five, six, seven, eight or greater number of leaflets 106. As shown in FIG. 1B, the leaflets 106 close toward a center 108 of the conduit 102 in the closed configuration. In an open configuration, blood may flow through the valve structure 104 with the leaflets 106 being forced toward an interior surface 110 of the conduit 102. The leaflets 106 may be coupled to the valve structure 104, and to the conduit 102, such that the interior surface 110 of the conduit 102 has a substantially smooth interior with substantially consistent interior diameter (e.g., sinus free and/or less than 5% thickness is added to a wall thickness of the conduit 102) as shown in FIG. 1B.

The substantially smooth interior surface 110 of the conduit 102 includes no bulging, inwardly or outwardly, of the flow surface (interior surface 110) of the conduit 102. The conduit 102 does not include a sinus. A sinus is a region of a conduit that has a larger inner diameter than a surrounding region. As shown in FIG. 1B, the conduit 102 does not include any sinuses.

In addition and as further described with reference to FIGS. 3-6, the interior surface 110 of the conduit 102 has not been mechanically altered for attachment of leaflets 106 to the conduit 102. More specifically, the interior surface 110 of the conduit 102 does not include any holes or other punctures that, in other devices, may be associated with a suture used for leaflet attachment. As further described with reference to FIGS. 3-6, the leaflets 106 are attached to the conduit 102 without puncturing the conduit 102 or otherwise mechanically altering the conduit 102 in order to attach the leaflets 106 thereto. Advantageously, the conduit 102 being free of mechanical alteration (e.g., no holes or suture) for attaching the leaflets 102 lessens the opportunity for thrombus formation by, for example, not altering blood flow through the conduit 102.

In certain embodiments, the interior surface 110 of the conduit 120 is diametrically constant and free of any macroscopic interruptions as shown in FIG. 1B. In addition, the leaflets 106 may be positioned within the conduit 102 at a longitudinal location along the length of the conduit 102 (e.g., as shown in FIG. 1A), and the conduit 102 is diametrically constant at the longitudinal location where the leaflets 106 are positioned and through adjacent proximal and distal portions of the conduit 102.

As shown in FIG. 1B, gaps 112 exist between each of the leaflets 106. The gaps 112 allow backflow through the conduit 102. The backflow lessens the opportunity for blood to stagnate behind the leaflet 106, which can lead to thrombus formation. The gaps 112 are sized such that leakage resulting from the backflow is minimal and does not otherwise increase strain on the patient's heart to pump blood through the conduit 102. The gaps 112 are associated with gaps 112 in the conduit 102, as shown in detail in FIGS. 4A-C.

The lack of sinuses, the lack of mechanical alteration (e.g., no mechanical coupling such as by suture, rivet, pin, staple, or similar attachment mechanism), and the gaps 112 between the leaflets 106 individually and in combination lessens the opportunity for formation. For example, the lack of mechanical alteration (e.g., no suture, rivet, pin, staple, or similar attachment mechanism) to couple the leaflet 106 to the conduit lessens the opportunity for turbulence in the blood flow through the conduit 102, which, as a result, lessens the opportunity for thrombus formation. In addition, the lack of sinuses in the conduit 102 lessens the opportunity for blood to stagnate within the conduit 102, which, as a result, lessens the opportunity for thrombus formation. Further, the gaps 112 between the leaflets allow backflow to wash out regions in the conduit 102 that potentially stagnate blood, which, as a result, lessens the opportunity for thrombus formation.

Figure 2:
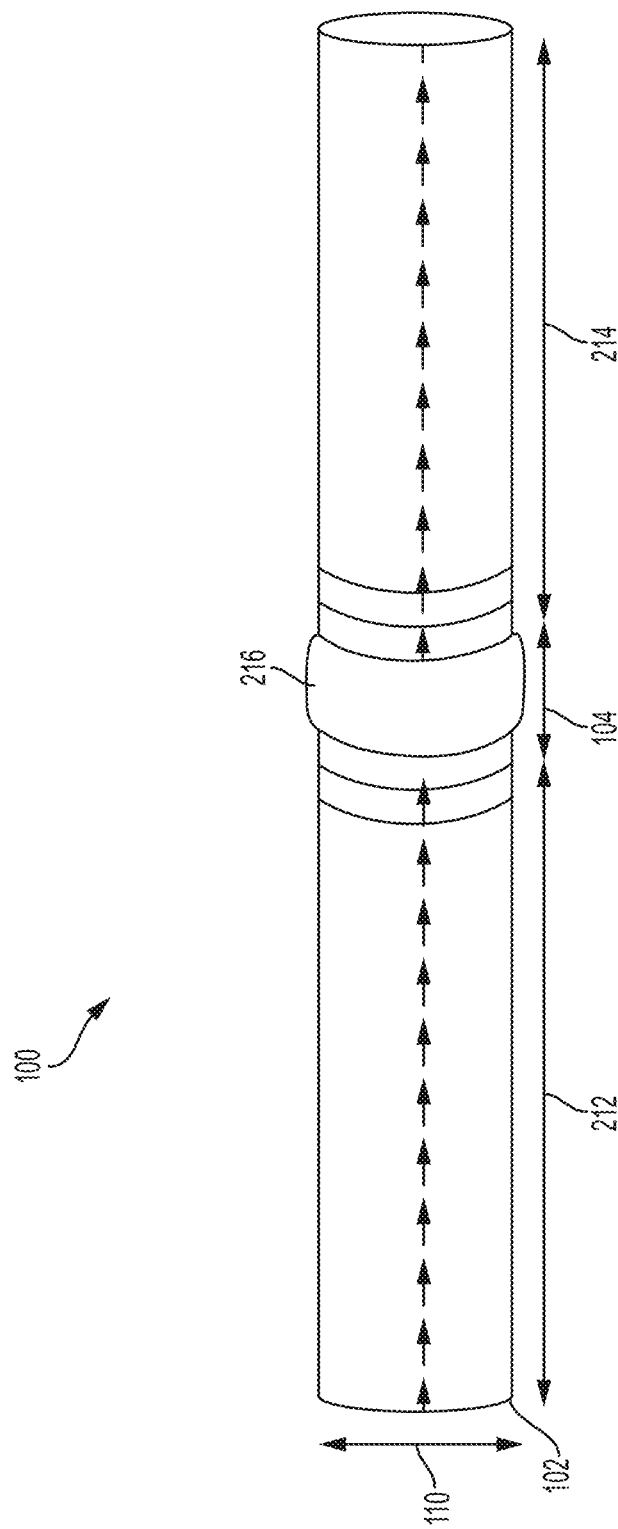
FIG. 2 is an illustration of another example valved conduit, in accordance with an embodiment.

FIG. 2 is an illustration of another example valved conduit 100, in accordance with an embodiment. The valved conduit 100 includes a conduit 102 and a valve 104. The conduit 102 includes an inflow portion 212 and an outflow portion 214. As indicate by the arrows on the conduit 102, the valve 104 is configured to allow blood flow through the conduit 102 from the inflow portion 212 to the outflow portion 214. The arrows may be a design feature printed on the conduit 102 to indicate the direction of blood flow within the conduit 102 to orient the physician for proper implantation. The arrows (a directional indicator) may be of a number of different shapes, sizes, lengths, or include other considerations.

As noted above with reference to FIG. 1, the valve 104 includes one or more leaflets (not shown). The leaflets may be coupled or attached to the valve 104. The term "coupled", as used herein, means joined, connected, attached, adhered, affixed, or bonded. The leaflet(s) are adhered (e.g., non-mechanically) to an exterior surface of the conduit 102 by an adhesive, thermal bonding, or chemical bonding. In this manner, the leaflet(s) are attached or coupled to the conduit 102 without puncturing or otherwise mechanically altering a surface of the leaflet(s) or the conduit 102 for attachment. In certain instances, the leaflets are attached, adhered, affixed, or bonded to the conduit 102 by an adhesive film 216. In addition, a suture may be used to attached the leaflet(s) to the exterior surface of the conduit 102 so long as the suture is arranged partially through the conduit 102 (e.g., not into the lumen of the conduit 102).

The adhesive film 216 may be a continuous or discontinuous layer wrapped about a circumference of the conduit 102. The adhesive film 216 may be placed, or wrapped about a circumference of the conduit 102, at a densified portion (discussed with reference to FIG. 3) of the conduit 102 and/or beyond the densified region provided it is within the valve region 350 of the conduit 102 to couple the leaflets 106 to the exterior surface of the conduit 102. In other embodiments, the adhesive film 216 can be placed in the valve region 350 of the conduit 102 and also beyond the valve region 350 of the conduit 102 and may in some embodiments cover the entire conduit 102.

Coupling or attaching the leaflet(s) to the exterior surface of the conduit 102 by, for example, an adhesive, thermal bonding, or chemical bonding maintains conduit diameter and effective valve orifice area (EOA) without long term anticoagulant therapy to prevent thrombus and/or tissue deposition. In addition, coupling the leaflet(s) to the conduit 102 in this manner assists in resistance to calcification and mineralization and minimizing of thrombosis formation.

Figure 3:
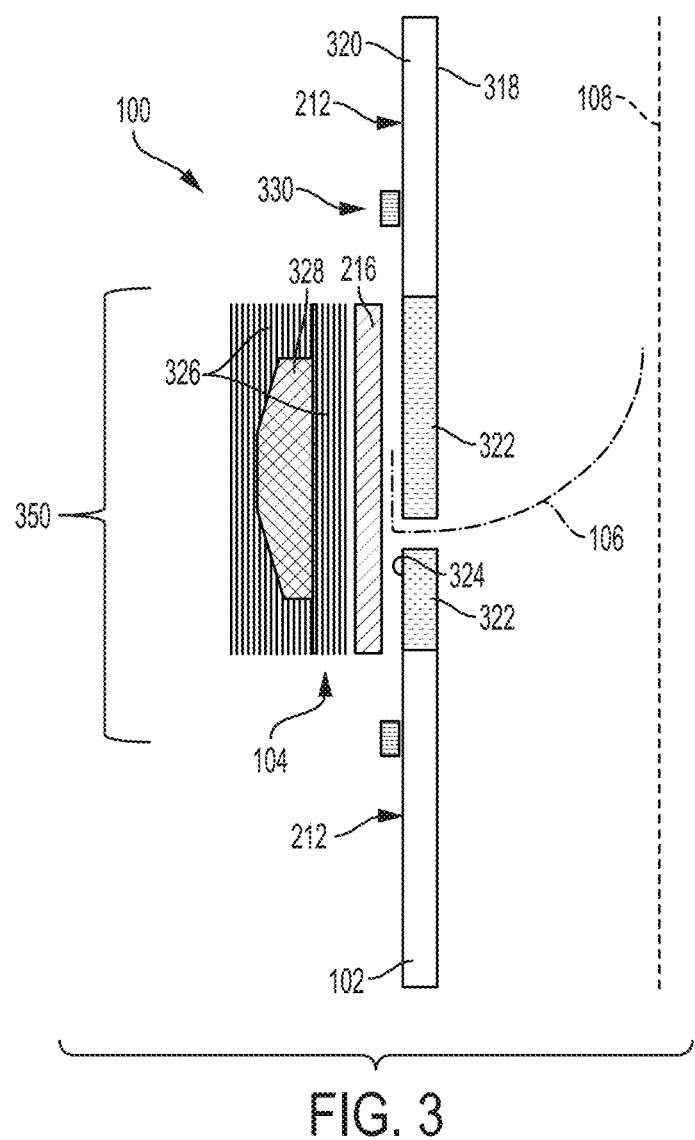
FIG. 3 is a cross-sectional illustration of another example valved conduit, in accordance with an embodiment.

FIG. 3 is a cross-sectional illustration of another example valved conduit 100, in accordance with an embodiment. The valved conduit 100 includes a conduit 102 having an interior surface 318, an exterior surface 320, a proximal (or inflow) portion 212, and a distal (or outflow) portion 214. The conduit 102 includes a leaflet attachment portion 322 having an opening 324 between the interior surface 318 and the exterior surface 320 of the conduit 102. The leaflet attachment portion 322 may be an integral portion of the conduit 102.

The valved conduit also includes a leaflet 106 that extends into the conduit 102 and toward the center 108 of the conduit. As shown in FIG. 3, the leaflet 106 is adhered to the exterior surface 320 of the conduit 102. The leaflet 106 may include portions that are arranged external to the conduit 102, through the opening 324, and within the conduit 102 as shown in FIG. 3. The leaflet 106 is adhered to the exterior surface 320 of the conduit 102 by an adhesive film 216. The adhesive film 216 may be arranged within the bounds of the leaflet attachment portion 322. In addition, the leaflet attachment portion 322 may be densified as compared to the proximal (or inflow) portion 212 and the distal (or outflow) portion 214 of the conduit 102.

The leaflet attachment portion 322 may be densified and/or rigidified such that the conduit 200 retains its shape during handling and use. Densification refers to a process of selectively making the material more dense at selected locations, such as by heating and/or pressure. In certain embodiments, the conduit 102 is formed from expanded Polytetrafluoroethylene (ePTFE). For ePTFE material that may be relatively porous, the densification process will reduce porosity and make the area more rigid.

The valved conduit 100 also includes a flexible film 326 arranged about the circumference of the conduit 102 and the adhesive film 216. The flexible film 326, in certain embodiments, may include one or more layers of the flexible film 326. The flexible film 326 may be wrapped multiple times about the conduit 102 and the adhesive film 216. The flexible film 326 may be wrapped as necessary to enhance the strength of the conduit 102 and/or the attachment of the leaflet 106 to the conduit 102. The adhesive film 216 may be placed, or wrapped about a circumference of the conduit 102, at the leaflet attachment portion 322 (e.g., discussed with reference to FIG. 3) of the conduit 102 and/or beyond the leaflet attachment portion 322 provided it is within a valve region 350 of the conduit 102 to couple the leaflets 106 to the exterior surface 320 of the conduit 102. In other embodiments, the adhesive can be placed in the valve region 350 of the conduit 102 and also beyond the valve region 350 of the conduit 102 and may in some embodiments cover the entire conduit 102.

The flexible film 326, for example, enhances longitudinal tensile strength of the conduit 102 by adding column strength to the conduit 102 and ensures that the leaflet 106 is secured within the conduit 102. In certain embodiments and as noted above, the conduit 102 may be ePTFE. Particularly suitable are ePTFE grafts having stretch/elastic behavior as they provide variable length without compromising surface smoothness including providing an uninterrupted luminal surface. In this regard, the exterior surface 320 of the conduit 102 can stretch for conform to the anatomy without kinking the interior surface 318 (luminal flow surface) of the conduit 102. The flexible film 326 may also be ePTFE with the adhesive film 216 being fluorinated ethylene propylene (FEP). By using the flexible film 326 and the adhesive film 216 in combination, the leaflet 106 may be bonded (e.g., thermally) to the conduit 102.

In certain embodiments, the valved conduit 100 may also include a support frame 328 coupled to the conduit 102 by the flexible film 326. The support frame 328 can prevent compression, or otherwise reduce compressibility of the conduit 102 and the valve 104 resulting from anatomical compression forces. In addition, the support frame 328, in certain embodiments, is formed of polyether ether ketone (PEEK). In these instances, the support frame 328 is not radiopaque, and therefore, allows a physician to better visualize the location of the leaflet 106 and the leaflet attachment portion 322 as compared if the support frame 328 was formed from other materials. Visualizing the leaflet 106 and/or the leaflet attachment portion 322 may enhance the ability of a physician to accurately locate and place the conduit 102 in a target location. In other instances, the support frame 328 is formed of a radiopaque material.

The support frame 328 may or may not be radiopaque. In certain instances, the valved conduit 100 may include one or more radiopaque markers 330 to assist in visualizing the valve region 350 of the conduit 102 post-procedure under fluoroscopic visualization. The one or more radiopaque markers 330 can be arranged adjacent to the leaflet 106 on the exterior surface 320 of the conduit 102. In certain embodiments and as shown in FIG. 3, the valved conduit 100 may include radiopaque markers 330 on either side, longitudinally, of the leaflet 106 and the leaflet attachment portion 322. In this manner, the physician has markers for placement of the leaflet 106 and the leaflet attachment portion 322 more particularly at the target location. The radiopaque markers 330, in certain embodiments, are continuous or discontinuous ribbons of radiopaque material (e.g., gold) wrapped about a circumference of the conduit 102.

Figure 4A:
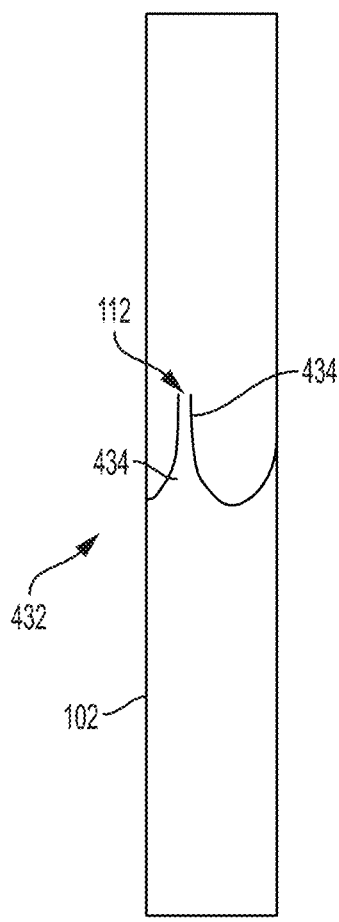
FIG. 4A is an illustration of an example cutting pattern for a conduit as used in a valved conduit, in accordance with an embodiment.

FIG. 4A is an illustration of an example cutting pattern 432 for a conduit 102 as used in a valved conduit, in accordance with an embodiment where a single conduit component is utilized. The cutting pattern 432 includes multiple separate slits 434 (e.g., creating the opening 324 shown in FIG. 3). The slits 434 correspond to the number of leaflets (not shown) that will be coupled to the conduit 102. As shown in further detail, for example, in FIGS. 6A-C, one or more leaflets may be arranged in the slits 434 with a portion of the leaflets being adhered to the conduit 102. As shown in FIG. 4A, the slits 434 in the cutting pattern 432 are not connected. Accordingly, the conduit 102 is not separated into multiple pieces during assembly and a single conduit component is utilized. Although two slits 434 are shown in FIG. 4A, the cutting pattern 432 may have additional slits (e.g., three slits for a tricuspid valve, four slits, etc.). The slits 434 may be formed by laser cutting, hand cutting, or other similar methods.

The slits 434 are separated by a gap 112. As noted above, the slits 434 correspond to the number of leaflets (not shown) that will be coupled to the conduit 102. The gap 112 correspond to separation between the leaflets within the conduit 102 (e.g., at a commissure post region). When the leaflets close (e.g., the valve is closed), there is a space between the leaflets as shown in FIG. 1. The slits 434 and the gaps 112 correspond to the number of leaflets that will be coupled to the conduit 102. The gaps 112 allow blood to wash-out regions behind the leaflets when the leaflet valve is closed. The backflow lessens the opportunity for blood to stagnate behind the leaflet, which can lead to thrombus formation. The gaps 112 are sized such that the leakage that results from the backflow is minimal and does not otherwise increase strain on the patient's heart to pump blood through the conduit 102.

Figure 4B:
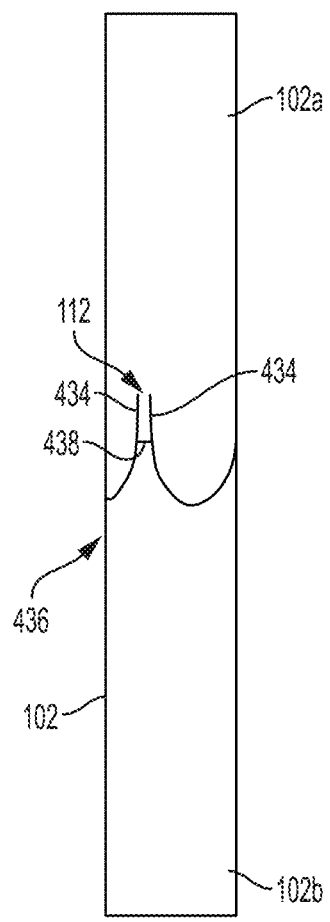
FIG. 4B is an illustration of another example cutting pattern for a conduit as used in a valved conduit, in accordance with an embodiment.

FIG. 4B is an illustration of another example cutting pattern 436 for a conduit 102 as used in a valved conduit, in accordance with an embodiment. The cutting pattern 436 includes multiple separate slits 434 with the number of slits corresponding to a number of leaflets (not shown) that will be coupled to the conduit 102. The cutting pattern 436 also includes a lateral cut 438 in the conduit 102 that allows for the conduit 102 to be split into two conduit components for assembly as shown as 102*a* and 102*b* in FIG. 4B. The lateral cut 438 is arranged near, adjacent to, or at a midpoint of a longitudinal portion of the slits 434. The lateral cut 438 and the slits 434 may be formed by laser cutting, hand cutting, or other similar methods. Although two slits 434 are shown in FIG. 4B, the cutting pattern 436 may have additional slits (e.g., three slits for a tricuspid valve, four slits, etc.).

The slits 434 and the lateral cut 438 correspond to the number of leaflets that will be coupled to the conduit 102. Similar to FIG. 4A, the slits 434 are separated by a gap 112. The gaps 112 correspond to separation between the leaflets within the conduit 102 (e.g., at a commissure post region). When the leaflets close (e.g., the valve is closed), there is a space between the leaflets as shown in FIG. 1. The gaps 112 allow blood to wash-out regions behind the leaflets when the leaflet valve is closed. The backflow lessens the opportunity for blood to stagnate behind the leaflet, which can lead to thrombus formation. The gaps 112 are sized such that the leakage that results from the backflow is minimal and does not otherwise increase strain on the patient's heart to pump blood through the conduit 102.

Figure 4C:
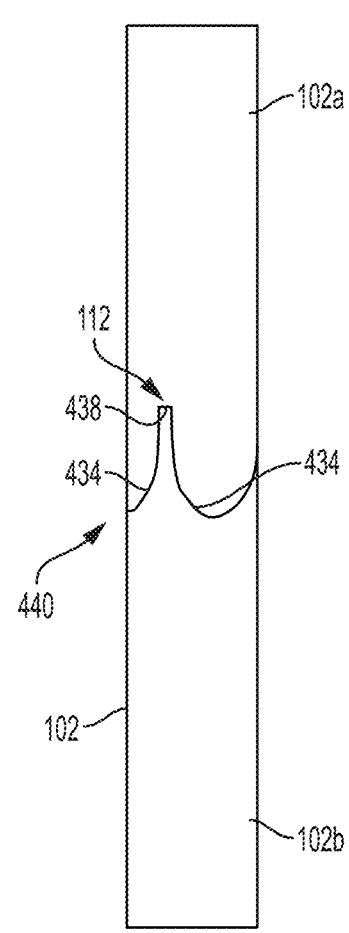
FIG. 4C is an illustration of another example cutting pattern for a conduit as used in a valved conduit, in accordance with an embodiment.

FIG. 4C is an illustration of another example cutting pattern 440 for a conduit 102 as used in a valved conduit, in accordance with an embodiment. The cutting pattern 440 includes multiple separate slits 434 with the number of slits corresponding to a number of leaflets (not shown) that will be coupled to the conduit 102. The cutting pattern 440 also includes a lateral cut 438 that is also a cut in the conduit 102 that allows for the conduit 102 to be cut into two conduit components for assembly as shown as 102*a* and 102*b* in FIG. 4C. The lateral cut 438 and the slits 434 may be formed by laser cutting, hand cutting, or other similar methods. Although two slits 434 are shown in FIG. 4B, the cutting pattern 440 may have additional slits (e.g., three slits for a tricuspid valve, four slits, etc.).

As noted above, the slits 434 and the lateral cut 438 correspond to the number of leaflets that will be coupled to the conduit 102. Similar to FIG. 4A, the slits 434 are separated by a gap 112. The gaps 112 correspond to separation between the leaflets within the conduit 102 when the valve is closed (e.g., maintaining the gap 112 at a commissure post region when the valve is closed).

Figure 5:
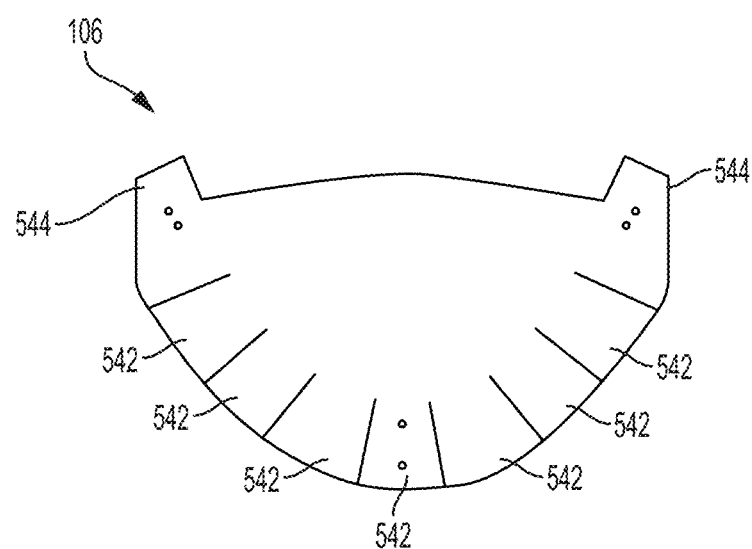
FIG. 5 is an illustration of an example leaflet that may be used in a valved conduit, in accordance with an embodiment.

FIG. 5 is an illustration of an example leaflet 106 that may be used in a valved conduit, in accordance with an embodiment. As shown in FIG. 5, the leaflet 106 may include multiple tabs 542. The tabs 542 may be formed by cutting portions of the leaflet 106 to separate the leaflet 106 into the tabs 542. As shown in further detail with reference to FIGS. 6A-C, the tabs 542 may be used to adhere the leaflet 106 to a conduit (not shown).

In certain embodiments, the leaflet 106 includes alignment tabs 544. The alignment tabs 544 are formed in the same manner as the tabs 542. The alignment tabs 544, when present in the leaflet 106, are used to interface with the conduit 102 to assist in aligning the leaflet 106 for attachment to the conduit 102.

The leaflet 106 may include, according to an embodiment, a composite material comprising an expanded fluoropolymer membrane, which comprises a plurality of spaces within a matrix of fibrils, and an elastomer, elastomeric material, or non-elastomeric material. It should be appreciated that multiple types of fluoropolymer membranes and multiple types of elastomer or elastomeric materials or non-elastomeric material can be combined to form a composite material while remaining within the scope of the present disclosure. It should also be appreciated that the elastomer or elastomeric material can include multiple elastomers and elastomeric materials, multiple types of non-elastomeric components, such as inorganic fillers, therapeutic agents, radiopaque markers, and the like while remaining within the scope of the present disclosure. In certain instances, the leaflet 106 may be a polymeric non-biological valve comprises a composite of ePTFE and a copolymer composed of tetrafluoroethylene (TFE) and perfluoromethyl vinyl ether (PMVE) (TFE-co-PMVE).

Figure 6C:
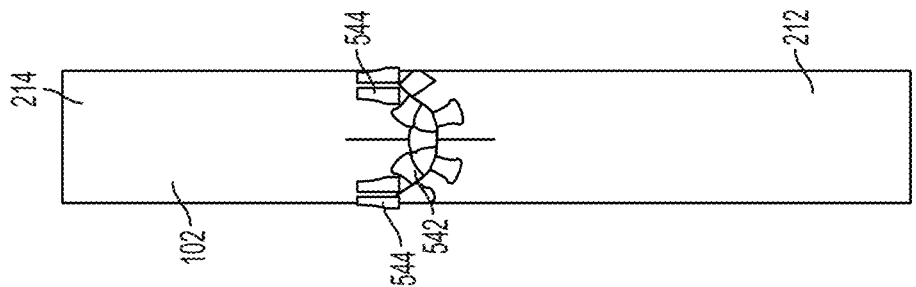
FIG. 6C is an illustration of another example step in attachment of the leaflet to the conduit, shown in FIGS. 6A-B.
Figure 6B:
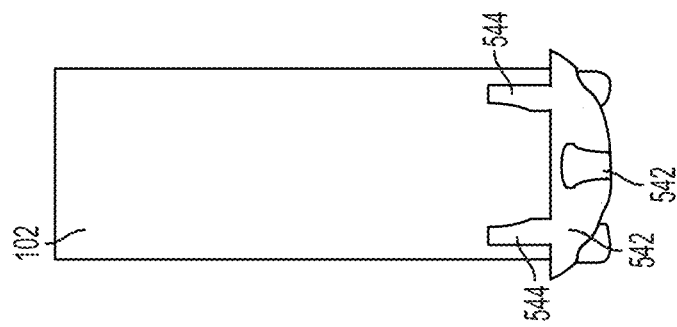
FIG. 6B is an illustration of another example step in attachment of the leaflet to the conduit, shown in FIG. 6A.
Figure 6A:
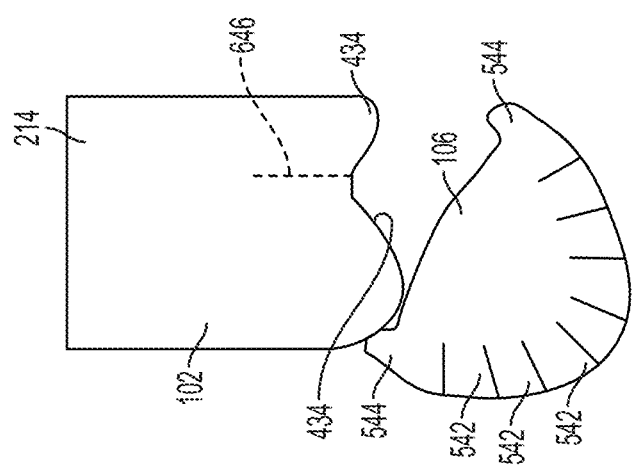
FIG. 6A is an illustration of an example step in attachment of a leaflet to a conduit, in accordance with an embodiment.

FIG. 6A is an illustration of an example step in attachment of a leaflet 106 to a conduit 102, in accordance with an embodiment. For ease of illustration, an upstream portion 214 of the conduit 102 is shown in FIG. 6A, however, as noted with reference to FIG. 4A, the conduit 102 and the leaflet 106 may be coupled together without separating the conduit 102 into multiple sections.

The leaflet 106 is aligned with a slit 434 in the conduit 102. As noted above, multiple leaflets 106 may be coupled to the conduit 102. For ease of illustration, FIGS. 6A-C illustrate attachment of a single leaflet 106 to the conduit 102. In certain embodiments, the conduit 102 includes an alignment line 646 that extends longitudinally along the conduit 102. The alignment line 646 facilitates aligning the leaflet 106 in the conduit 102. The leaflet 106, in certain embodiments, includes alignment tabs 544 that are arranged within the alignment line 646 to ensure that the geometry and alignment of the leaflet 106 within the conduit 102 is proper. The alignment line 646 may be a gap in the conduit 102 into which the alignment tabs 544 are arranged.

Once the leaflet 106 is aligned with the slit 434, the tabs 542 may be folded down onto an exterior surface of the conduit 102. As shown in FIG. 6B, the alignment tabs 544 may be folded inward circumferentially.

As shown in FIG. 6C, the tabs 542 may be folded in different directions. Alternating tabs 542, for example, may be folded onto the exterior surface of the proximal (or inflow) portion 212 and the distal (or outflow) portion 214 of the conduit 102. The tabs 542 (and alignment tabs 544) may be attachment sections of the leaflet 106, which may be adhered to the exterior surface of the conduit 102 by an adhesive, thermal bonding, or chemical bonding (e.g., as detailed above with reference to FIGS. 2-3). Sections of the leaflet 106 extend through an opening (e.g., as shown in FIG. 3) in the conduit 102 between the proximal (or inflow) portion 212 and the distal (or outflow) portion 214. The remaining portions of the leaflet 106 within the conduit 102 function as the valve in the valved conduit 100.

Figure 7C:
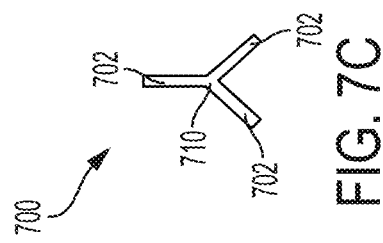
FIG. 7C is a top view of the packaging insert, shown in FIGS. 7A-B, in a folded configuration.
Figure 7B:
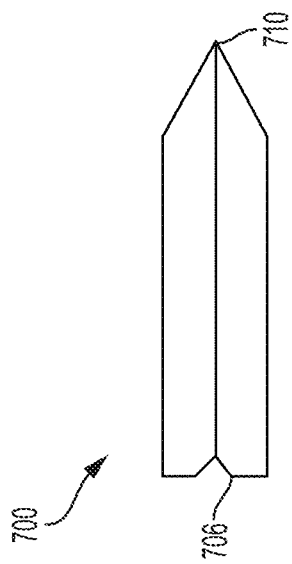
FIG. 7B is a side view of the packaging insert, shown in FIG. 7A, in a folded configuration.
Figure 7A:
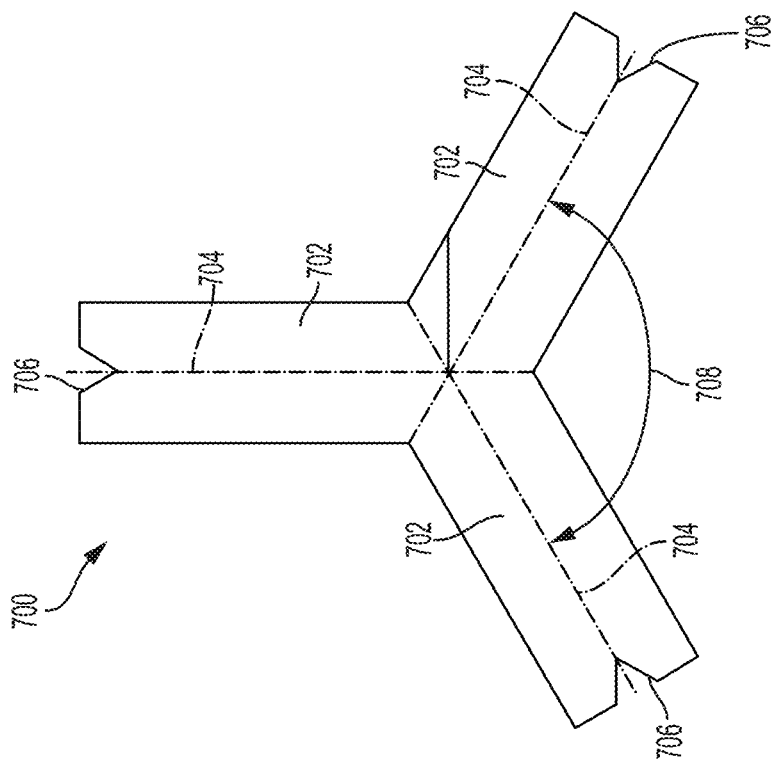
FIG. 7A is an illustration of an example packaging insert for a valved conduit in an unfolded configuration, in accordance with an embodiment.

FIG. 7A is an illustration of an example packaging insert 700 for a valved conduit in an unfolded configuration, in accordance with an embodiment. The packaging insert 700 may be used with the valved conduits discussed herein to ensure that the valved conduits are not damaged during delivery and/or storage of the valved conduit. The packaging insert 700 may be arranged in the lumen of the conduit 102 to hold the leaflet 106 or leaflets 106 apart.

As shown in FIG. 7A, the packaging insert 700 includes an unfolded configuration. The packaging insert 700 includes multiple supports 702, with the supports 702 being equal to the number of leaflets 106 that are included with the valved conduit. The supports 702 include score lines 704 to facilitate folding of the supports 704 from the unfolded configuration. The supports 702 may also include notches 706 for fold alignment. To transition to the folded configuration, shown in FIGS. 7B-C, the supports 702 should be folded along the score lines 704 and creased. The supports 702 may be spaced equally apart by an angle 708. In embodiments where the packaging insert 700 includes three supports 702, the angle 708 is approximately 120 degrees.

As shown in FIGS. 7B-C, the packaging insert 700 forms a tip 710 in the folded configuration. In the folded configuration, the leaflets 106 can rest on the supports 702 to maintain separation between the leaflets 106.

The conduits discussed herein may be a synthetic conduit with at least one flexible synthetic valve leaflet attached to the synthetic conduit. Prior to implantation, the synthetic valve leaflet and/or the synthetic conduit that may be rinsed in saline and does not require pre-clotting. Subsequently, the synthetic valve leaflet and the synthetic conduit may be surgically implanted. The synthetic valve leaflet and the synthetic conduit may be a replacement of the native pulmonary valve or of a previously implanted pulmonary valved conduit where partial or complete reconstruction of the right ventricular outflow tract and/or main pulmonary artery is desired. In certain instances, installation of the synthetic valve leaflet and the synthetic conduit includes identifying the inflow and outflow regions of the conduit, accessing the intended position with respect to the coronary arteries to assure there is no risk of coronary compression when implanted, and optionally trimming the inflow and or outflow conduit, while under moderate tension, to the appropriate length for implantation.

In certain embodiments, the conduits discussed herein include an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure, such as pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In various examples, any of the leaflet constructs described herein (e.g., leaflet construct) may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In other examples, such leaflet construct is formed of a natural material, such as repurposed tissue, including bovine tissue, porcine tissue, or the like.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct further comprises a layer of an elastomer and/or an elastomeric material and/or a non-elastomeric material on the composite material. In accordance with some examples, the composite material comprises porous synthetic polymer membrane by weight in a range of about 10% to 90%

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkylvinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet construct is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet construct 300 further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer material made from porous ePTFE membrane, for instance as generally described in U.S. Pat. No. 7,306,729 to Bacino.

The expanded fluoropolymer membrane, used to form some of the composites described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

Sample Testing

Figure 8:
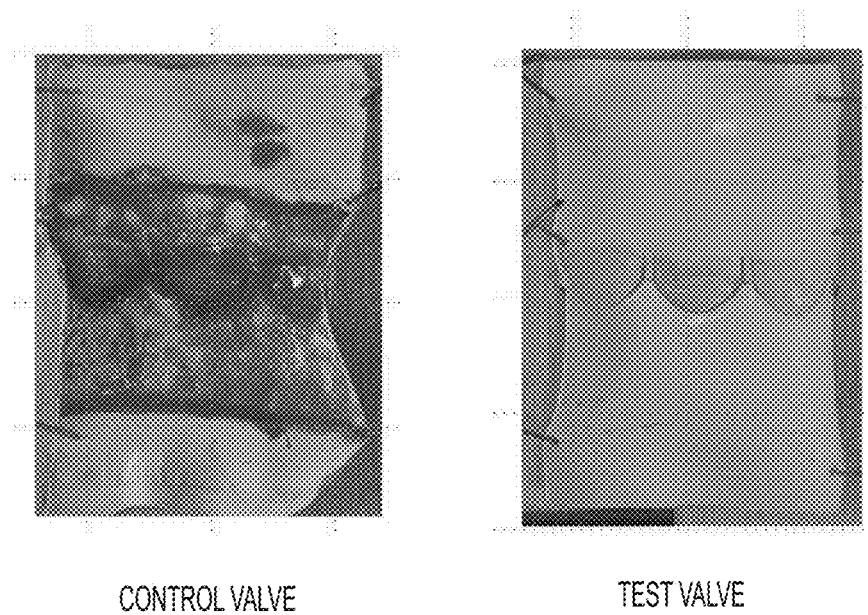
FIG. 8 shows an example thrombogenic response of a prior art device compared to a device in accordance with embodiments of the present disclosure.

A valved conduit ("Control Valve") includes leaflets attached by suturing and with a sinus at the valve region of the conduit in accordance with US Patent Publication No. 2016/0100939, "Valved Conduit", W. L. Gore & Associates, Inc., Armstrong et. al., filed Oct. 12, 2015. Another valved conduit ("Test Valve") may be made in accordance with embodiments of this disclosure and include leaflets attached non-mechanically, with an interior surface that is diametrically constant and free of any macroscopic interruptions, without a sinus at the valve region of the conduit. FIG. 8 is illustrative of the performance of such a Control Valve and a Test Valve under simulated operating conditions, including exposure to blood. As shown in FIG. 8, the Control Valve exhibits a relatively larger thrombogenic response as compared to Test Valve when exposed to blood for approximately 3 hours. The Control valve and the Test Valve showed similar thrombogenic responses at different exposure times. As shown, the Control Valve exhibited a significantly larger thrombogenic response as compared to Test Valve. Such testing is illustrative of the relative reduction in thrombogenicity achievable according to embodiments of this disclosure.

It should be understood that although certain methods and equipment are described below, other methods or equipment determined suitable by one of ordinary skill in the art may be alternatively utilized.

Test Methods

An non-limiting example of a suitable test method for evaluating thrombogenic response of such valved conduits includes utilizing an in vitro, laboratory closed blood loop (e.g., heparinized porcine blood) with pulsatile flow to cause actuation of a sample valved conduit for a desired time (e.g., greater than one hour). The sample valved conduit can then be removed from the closed blood loop and cut open for visual examination and assessment of thrombus formation.

Inventive features of this disclosure have been described above both generically and with regard to specific embodiments. It will be apparent to those skilled in the art that various modifications and variations can be made in the embodiments without departing from the scope of the disclosure. Thus, it is intended that the embodiments cover the modifications and variations of this disclosure provided they come within the scope of the appended claims and their equivalents.

What is claimed is:

1. A valved conduit comprising:
    a conduit having and an exterior surface and an interior surface defining a lumen; and
    at least one leaflet extending through an opening in the conduit to define an external portion extending along the exterior surface of the conduit and an internal portion extending into the lumen of the conduit, wherein the internal portion is operable as a one-way valve that opens to permit blood to flow through the lumen and closes to occlude blood flow through the lumen, wherein the external portion is nonmechanically and suturelessly attached to the exterior surface of the conduit by an adhesive film.

2. The valved conduit of claim 1, wherein the conduit is free of sinuses.

3. The valved conduit of claim 1, wherein the conduit is free of mechanical coupling.

4. The valved conduit of claim 1, wherein the adhesive film is arranged about a circumference of the conduit.

5. The valved conduit of claim 1, further comprising a flexible film arranged about a circumference of the conduit and the adhesive film.

6. The valved conduit of claim 5, wherein the flexible film includes expanded Polytetrafluoroethylene (ePTFE) and the adhesive film comprises fluorinated ethylene propylene (FEP).

7. The valved conduit of claim 5, further comprising a support frame coupled to the conduit by the flexible film.

8. The valved conduit of claim 7, wherein the support frame is formed of Polyether ether ketone (PEEK).

9. A valved conduit comprising:
- a conduit having and an exterior surface and an interior surface defining a lumen;
- at least one leaflet extending through an opening in the conduit to define an external portion extending along the exterior surface of the conduit and an internal portion extending into the lumen of the conduit, wherein the internal portion is operable as a one-way valve that opens to permit blood to flow through the lumen and closes to occlude blood flow through the lumen, wherein the external portion is attached to the exterior surface of the conduit by adhesive, thermal bonding, or chemical bonding; and
- at least one radiopaque marker arranged adjacent to the at least one leaflet on the exterior surface of the conduit.

10. The valved conduit of claim 1, wherein the interior surface of the conduit is diametrically constant and free of any macroscopic interruptions.

11. The valved conduit of claim 1, wherein the at least one leaflet is positioned within the conduit at a longitudinal location along a length of the conduit, and the conduit is diametrically constant at the longitudinal location where the at least one leaflet is positioned and through adjacent proximal and distal portions of the conduit.

12. The valved conduit of claim 1, wherein the at least one leaflet is non-mechanically and suturelessly coupled to the exterior surface of the conduit.

13. The valved conduit of claim 1, wherein the external portion of the at least one leaflet comprises two or more tabs and wherein the two or more tabs are coupled to the exterior surface of the conduit.

14. A valved conduit comprising: a conduit having and an exterior surface and an interior surface defining a lumen; and
- at least one leaflet extending through an opening in the conduit to define an external portion extending along the exterior surface of the conduit and an internal portion extending into the lumen of the conduit, wherein the internal portion is operable as a one-way valve that opens to permit blood to flow through the lumen and closes to occlude blood flow through the lumen, wherein the external portion is attached to the exterior surface of the conduit by adhesive, thermal bonding, or chemical bonding;

wherein:
- the external portion of the at least one leaflet comprises two or more tabs coupled to the exterior surface of the conduit; and
- the two or more tabs are folded in an alternating pattern towards a conduit proximal portion and towards a conduit distal portion.

15. The valved conduit of claim 14, wherein the two or more tabs comprises one or more alignment tabs and the conduit comprises one or more alignment lines on the exterior surface of the conduit, wherein each of the one or more alignment tabs is located at one of the one or more alignment lines.

16. The valved conduit of claim 1, wherein the at least one leaflet comprises a plurality of leaflets and the opening in the conduit comprises a plurality of U-shaped slits in the conduit, wherein each of the at least one leaflet extends through one of the plurality of U-shaped slits.

* * * * *